United States Patent [19]

Leonard

[11] 4,333,567
[45] Jun. 8, 1982

[54] PLATE FOR PACKAGING DENTAL ROOT-CANAL INSTRUMENTS

[75] Inventor: Henri Leonard, Besancon, France

[73] Assignee: Micro-Mega S.A., France

[21] Appl. No.: 135,286

[22] Filed: Mar. 31, 1980

[30] Foreign Application Priority Data

May 31, 1979 [FR] France ................................ 79 14659

[51] Int. Cl.³ ............................................ B65D 75/42
[52] U.S. Cl. .................................. 206/368; 206/366; 206/370; 220/345
[58] Field of Search ............... 206/368, 569, 570, 571, 206/363, 364, 365, 366, 369, 370, 528, 529, 534.1, 534.2, 538, 438; 220/20, 21, 23.8, 345

[56] References Cited

U.S. PATENT DOCUMENTS

| | | | |
|---|---|---|---|
| 3,049,224 | 8/1962 | Fredette et al. | 220/345 X |
| 3,207,302 | 9/1965 | Hobbs | 206/366 |
| 3,759,375 | 9/1973 | Nappi | 206/370 |
| 3,833,143 | 9/1974 | Starkermann et al. | 220/345 |
| 4,153,160 | 5/1979 | Leigh | 220/345 X |

Primary Examiner—Steven M. Pollard
Attorney, Agent, or Firm—Robert E. Burns; Emmanuel J. Lobato; Bruce L. Adams

[57] ABSTRACT

This plate for packaging dental root-canal instruments comprises a support formed with recesses adapted to receive the instruments and a protection cover which is a slide fit on the plate. The recesses consist of parallel elongated cavities extending at a short distance from, and at right angles to a longitudinal edge of the support, and comprise each an extension in the form of a neck towards the opposite longitudinal edge. The support also comprises a flat central area somewhat recessed in relation to the bottoms of the necks in order to facilitate the gripping of the instruments' shanks.

4 Claims, 4 Drawing Figures

U.S. Patent     Jun. 8, 1982     4,333,567
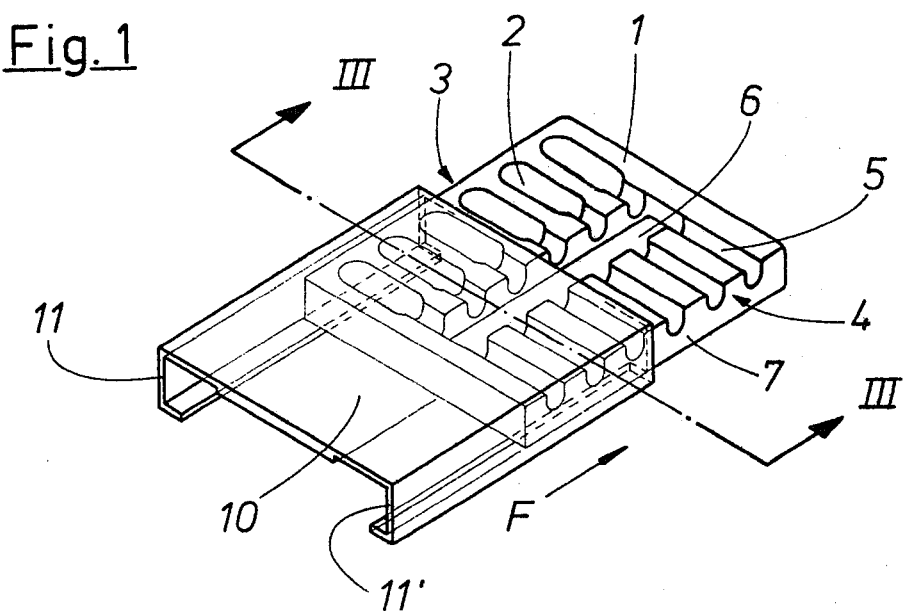
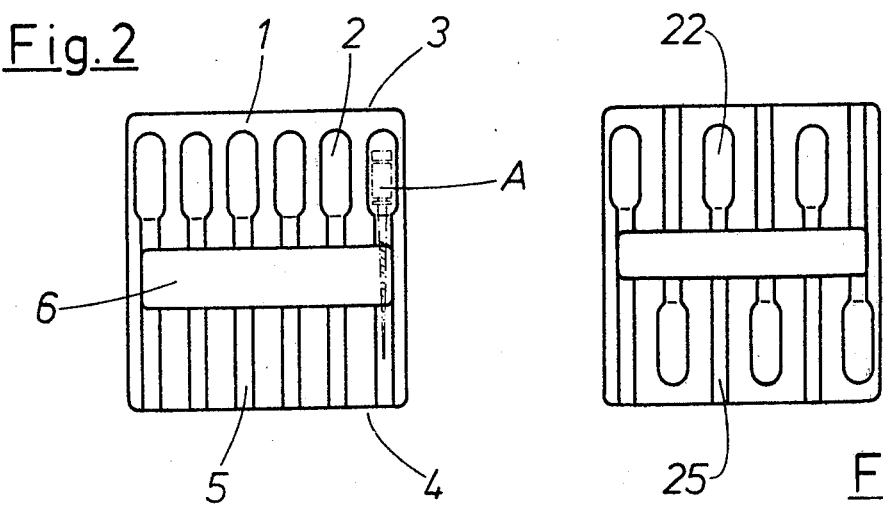
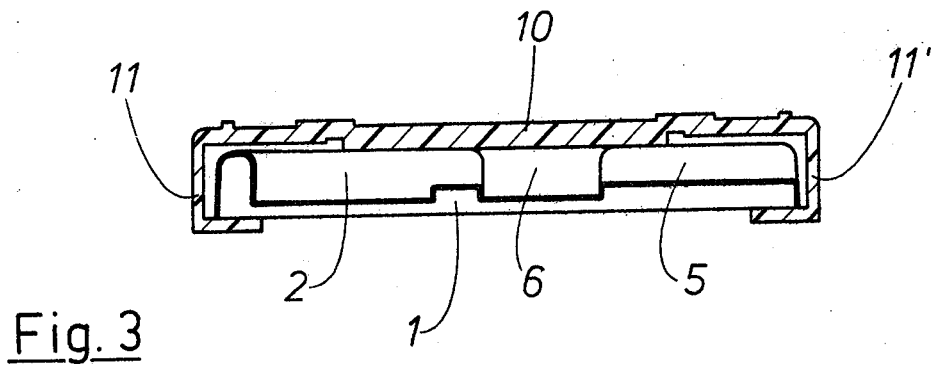

PLATE FOR PACKAGING DENTAL ROOT-CANAL INSTRUMENTS

BACKGROUND OF THE INVENTION

The present invention relates in general to means, in the form of a recessed plate, for packaging dental root-canal instruments, and more particularly to a plate for packaging dental nerve broaches or extractors or like instruments comprising a shank or handle, this plate package comprising on the one hand a support on which the instruments are disposed in parallel relationship into spaced, separate recesses, and on the other hand a protection cover which is a slide fit on said support.

As a rule, dental root-canal instruments such as nerve broaches comprise a shank of relatively small diameter, to which a cylindrical handle can be fixed, this handle having diameter and length sufficient to afford a proper gripping thereof. These instruments are relatively fragile and delicate to handle; therefore, they must be so packed as to meet all the necessary safety requirements while permitting their easy handling notwithstanding their relatively small dimensions.

SUMMARY OF THE INVENTION

It is the essential object of the present invention to provide plate means for packaging dental root-canal instruments of this character, which are capable of meeting all the above-mentioned safety and easy-handling requirements well known in the art.

To this end, the dental root-canal instrument packaging plate according to this invention is characterized in that the aforesaid support, made preferably of light-weight material, has formed therein a plurality of recesses constituting a series of elongated cells projecting from the rear face of the plate and adapted to receive the shank of an instrument, said recesses extending at right angles to the longitudinal edges of the support and within a short distance therefrom, each recess having an extension, towards the opposite longitudinal edge, in the form of a groove adapted to receive the slender shaft of the instrument, the continuity of said grooves being broken by a flat longitudinal central area of which the bottom is somewhat recessed in relation to the groove bottoms, that the support further comprising lateral edges of a height at least equal to, or greater than, the depth of said recesses, at least along the two longitudinal edges of the support, and that the protection cover is provided with a pair of opposite longitudinal edges bent to a U-shape and adapted to be slidably engaged by the longitudinal edges of the support.

This packaging device is extremely advantageous, notably from the point of view of cost, since according to a preferred form of embodiment of the invention the support may be molded from a suitable plastic material.

In addition, due to the slide fit of the protection cover with respect to the longitudinal edges of the support, the practitioner can uncover the instruments one by one, so that the risk of allowing all the instruments to fall inadvertently is safely precluded.

BRIEF DESCRIPTION OF THE DRAWING

FIG. 1 is a perspective view of the package plate according to this invention, the sliding protection cover being partly removed therefrom;

FIG. 2 is a plane view from above of the support alone, with an instrument shown in phantom lines;

FIG. 3 is a section taken along the line III—III of FIG. 1, showing the complete plate with its cover, and FIG. 4 is a plane view illustrating a modified form of embodiment of the support.

DESCRIPTION OF THE PREFERRED EMBODIMENTS

The packaging plate comprises essentially a support 1, notably of suitable thin transparent plastics, formed by molding, in which a series of parallel recesses 2 are formed. As clearly shown in FIG. 3, these recesses 2 project from the bottom or rear face of the support, have an elongated configuration and extend within a short distance from, and at right angles to, one of the longitudinal edges 3 of the support; each recess 2 has an extension towards the opposite longitudinal edge 4 of the support, in the form of a groove 5 somewhat shallower than the corresponding recess 2. Furthermore, in a substantially central area, the support 1 comprises a flat longitudinal portion 6 having its bottom either level with, or preferably deeper than, the bottom of each groove 5.

On the other hand, the support 1 has formed on its four sides lateral depending skirt elements 7 of a height at least equal to or greater than the depth of recesses 2; thus, when the support 1 is laid upon a flat surface, it bears on its peripheral skirt elements 7.

A protection cover 10 (FIG. 1) is adapted to fit on the support 1 by slidably engaging the longitudinal edges thereof. To this end, the cover 10 comprises two longitudinal edges 11,11' bent twice, i.e. downwardly and inwardly, to provide a pair of mutually facing U-shaped elements constituting slideways engageable by the longitudinal edges 3 and 4 of support 1. As seen in FIG. 10, a longitudinally extending central portion of the cover engages the upper face of the support 1 to retain the instruments in the recesses, while side portions of the cover are recessed from the upper surface of the support to reduce friction, save material and provide a certain flexibility.

Preferably, the protection cover 10 consists of rigid transparent plastics, in contrast to the support 1 consisting preferably of a relatively thin material, such as a thermoplastic material which may be transparent or not. In any case and preferably, one of the two elements, cover or support, is transparent so that the instruments kept therein can be seen from the outside without having to open the protection cover.

The dental root-canal instruments A, notably nerve extractors, are disposed in the support 1 in the manner illustrated in phantom lines in FIG. 2. Thus, the shank of the instrument for attachment to a tool or handle is disposed into a recess 2 and the slender shaft fitted thereto rests in the groove extension 5 across the flat area 6. Thus, the shaft portion overlying this flat area 6 is easily accessible for the practitioner. On the other hand, when the practitioner wants to grip an instrument, it is unnecessary for him to uncover all the instruments by pulling off the cover 10 completely, since he can advantageously uncover only one or two recesses 2.

In a modified form of embodiment of the support, as illustrated in FIG. 4, the recesses 22 are disposed head to tail, so that on a same side of the support the recesses 22 alternate with grooves 24 and it is thus possible to increase the number of instruments, given a same length of the support 1, in comparison with the arrangement of FIGS. 1 to 3.

Preferably, the support 1 is adapted to receive six instruments, but this number is not a limiting factor, since ten, twelve or any other suitable number of instruments can be contemplated.

What is claimed is:

1. A container for packaging and dispensing root-canal instruments, notably nerve broaches, each having a shorter, thicker shank portion and a longer slender shaft portion, said container comprising;

a generally rectangular support having opposite side edges and opposite end edges, said support being formed of thin light material to provide an upper face and a plurality of spaced identical cavities formed in said upper face and extending parallel to one another and to end edges of said support, each of said cavities comprising a shorter, deeper, wider recess shaped and dimensioned to receive said shank portion of one of said instruments, said recess being located near one side edge of said support, and a longer, shallower and narrower groove shaped and dimensioned to receive said slender shaft portion of said instrument, said groove extending from said recess to the opposite side edge of said support, a central longitudinally extending channel formed in said upper face and extending substantially the full length thereof, said channel intersecting said grooves and having a depth greater than the depth of said grooves and a width to receive finger tips of a user, said support having at opposite side edges thereof depending skirt elements extending down from said upper face and having a height at least equal to the depth of said recesses, and a rigid cover molded of plastic material and comprising a top having a longitudinally extending central portion only engaging said upper face of said support while side portions of said top are recessed from the upper face of said support, and opposite side flanges extending down from said top outwardly of said side edges of said support and having inturned lower edge portions engaging under lower edges of said skirt portions of said support, said cover being thereby slidable longitudinally of said support to uncover individually instruments in said cavities, at least one of said support and cover being transparent so that said instruments can be seen.

2. A container according to claim 1, in which said recesses of alternate cavities are disposed adjacent one side edge of said support while recesses of intervening cavities are disposed adjacent the opposite side edge of said support.

3. A container according to claim 1, in which said support is formed of thin transparent thermoplastic material.

4. A container according to claim 1, in which said rigid cover is molded of transparent plastic material.

* * * * *